US006674523B2

United States Patent
Kawamorita et al.

(10) Patent No.: US 6,674,523 B2
(45) Date of Patent: Jan. 6, 2004

(54) PRE-VIEWING INSPECTION METHOD FOR ARTICLE AND DEVICE THEREFOR

(75) Inventors: Yoichi Kawamorita, Kanagawa (JP); Ryozo Fukuda, Ibaraki (JP); Kazuya Tokuda, Ibaraki (JP); Kenji Muranaka, Ibaraki (JP); Shoshin Igarashi, Ibaraki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/910,048

(22) Filed: Jul. 23, 2001

(65) Prior Publication Data
US 2002/0021123 A1 Feb. 21, 2002

(30) Foreign Application Priority Data
Jul. 27, 2000 (JP) ........................................ 2000-227334

(51) Int. Cl.[7] .............................................. G01N 21/00
(52) U.S. Cl. ................ 356/237.2; 356/237.1; 356/237.3; 356/237.4
(58) Field of Search .................... 356/237.1, 237.2, 356/237.3, 237.4, 237.5

(56) References Cited

U.S. PATENT DOCUMENTS

| | | | | |
|---|---|---|---|---|
| 4,383,263 | A | | 5/1983 | Ozawa et al. ............... 346/140 |
| 4,505,585 | A | * | 3/1985 | Yoshikawa et al. ....... 356/237.2 |
| 4,803,336 | A | * | 2/1989 | Myer ...................... 219/121.68 |
| 4,968,998 | A | | 11/1990 | Allen ......................... 346/140 |
| 5,657,891 | A | | 8/1997 | Bilani et al. ................. 220/256 |
| 5,801,965 | A | * | 9/1998 | Takagi et al. ............. 356/237.1 |
| 5,985,680 | A | * | 11/1999 | Singhal et al. .............. 356/614 |
| 6,118,540 | A | * | 9/2000 | Roy et al. ................ 356/237.5 |
| 6,148,097 | A | * | 11/2000 | Nakayama et al. ......... 382/141 |
| 6,250,251 | B1 | * | 6/2001 | Akiyama et al. ......... 118/723 E |
| 6,295,129 | B1 | * | 9/2001 | Bjork ........................... 356/430 |
| 6,476,913 | B1 | * | 11/2002 | Machida et al. ............ 356/394 |

FOREIGN PATENT DOCUMENTS

| | | |
|---|---|---|
| EP | 0 641 594 | 3/1995 |
| EP | 0 646 465 | 4/1995 |
| EP | 0 684 136 | 11/1995 |
| EP | 0 803 364 | 10/1997 |
| EP | 0 906 830 | 4/1999 |
| GB | 2 186 365 | 8/1987 |
| JP | 63-73139 | 4/1988 |
| JP | 04-069563 | 3/1992 |

(List continued on next page.)

OTHER PUBLICATIONS

European Search Report dated Jul. 17, 2003 (Ref. No. 01128522.8).

Primary Examiner—Michael P. Stafira
Assistant Examiner—Juan D Valentin
(74) Attorney, Agent, or Firm—Fitzpatrick, Cella, Harper & Scinto

(57) ABSTRACT

A pre-viewing inspection method and apparatus for inspecting an inspection article prior to visual inspection thereof, the inspection article being an electrophotographic member, such as an electrophotographic photosensitive member. The method (apparatus) comprises a defect signal detecting step (means) of detecting a defect signal based on a defect state of the inspection article, a detailed defect information generating step (means) of generating detailed defect information based on the defect signal detected in the defect signal detecting step, the detailed defect information including defect position information, and a detailed defect information visualizing step (means) of visualizing, on the inspection article, the detailed defect information generated in the detailed defect information generating step. The visualizing step (means) includes a printing step (means) executed with a laser light, wherein the detailed defect information visualizing step visualizes the detailed defect information by printing the detailed defect information on a longitudinal extension of a defect position on the inspection article, based on the defect position information.

22 Claims, 4 Drawing Sheets

FOREIGN PATENT DOCUMENTS

| | | |
|---|---|---|
| JP | 07-083849 | 3/1995 |
| JP | 7-218442 | 8/1995 |
| JP | 10-277912 | 10/1998 |
| JP | 2935881 | 6/1999 |
| JP | 2967291 | 8/1999 |
| JP | 11-319943 | 11/1999 |
| JP | 11-319944 | 11/1999 |
| JP | 2000-51937 | 2/2000 |
| JP | 2000-097873 | 4/2000 |
| JP | 2000-146920 | 5/2000 |

* cited by examiner

PRE-VIEWING INSPECTION METHOD FOR ARTICLE AND DEVICE THEREFOR

BACKGROUND OF THE INVENTION

1. Field of the Invention

The present invention relates to a pre-viewing inspection method for an article prior to visual inspection and a device therefor.

2. Related Background Art

In conventional manufacturing processes for various products, various inspection steps are provided in order to prevent a product having serious defects and not suitable for use, namely a defective product, from being forwarded to the market. In such inspection steps, the inspection by inspection devices is often insufficient for the following reasons and visual inspection by an inspector is adopted in many cases.

Defects in an inspection article do not necessarily lead to practical drawbacks, depending not only on their area or volume but also on their shape and nature. Stated differently, there are many defects which do not have practical influence, and it is unnecessary to discard an article with a defect having no practical influence. Also there is no inspection device capable of immediately evaluating the influence of the defects of such various forms on the practical use. Furthermore, an inspection device may erroneously identify a defect that in fact does not exist. These reasons lead to the necessity for the visual inspection by an inspector. Inspection devices have been improved in their ability in resolution for detecting finer defects and are provided with a logic circuit for judging whether an article is usable or not, but the judgment at the boundary level is entrusted to an inspector as stated above.

The visual inspection by an inspector is a visual inspection in which an inspector inspects defects in articles on which it is difficult for an inspecting device to judge whether the article are usable or not, and determines whether the article is usable or not, on the basis of comparison with criteria of defects or empirical rules.

In recent years, however, higher quality has been required for the articles to be inspected, and the defects to be judged by an inspector have become smaller and smaller. For this reason, the burden on such an inspection has increased, resulting in a deterioration in the inspection efficiency or inspection errors by an inspector in the final judgment.

SUMMARY OF THE INVENTION

The object of the present invention is to provide a pre-viewing inspection method (or an inspection method prior to visual inspection) for assisting the visual inspection which has been principally directed to detection of minute defects and improving the efficiency and precision of the inspection, and a device therefor.

The above-mentioned object can be attained, according to the present invention, by a pre-viewing inspection method for an inspection article, comprising:

- a defect signal detection step of detecting a defect signal based on a defect state of the article;
- a detailed defect information generation step of generating detailed defect information based on the defect signal detected in the defect signal detection step; and
- a detailed defect information visualization step of visualizing the detailed defect information, generated by the detailed defect information generation step, on the inspection article.

According to the present invention, a pre-viewing inspection device (or an inspection device prior to visual inspection) for an inspection article is provided comprising:

- defect signal detection means for detecting a defect signal based on a defect state of the article;
- detailed defect information generation means for generating detailed defect information based on the defect signal detected by the defect signal detection means; and
- detailed defect information visualization means for visualizing the detailed defect information, generated by the detailed defect information generation means, on the inspection article.

DETAILED DESCRIPTION OF THE PREFERRED EMBODIMENTS

Figure 1:
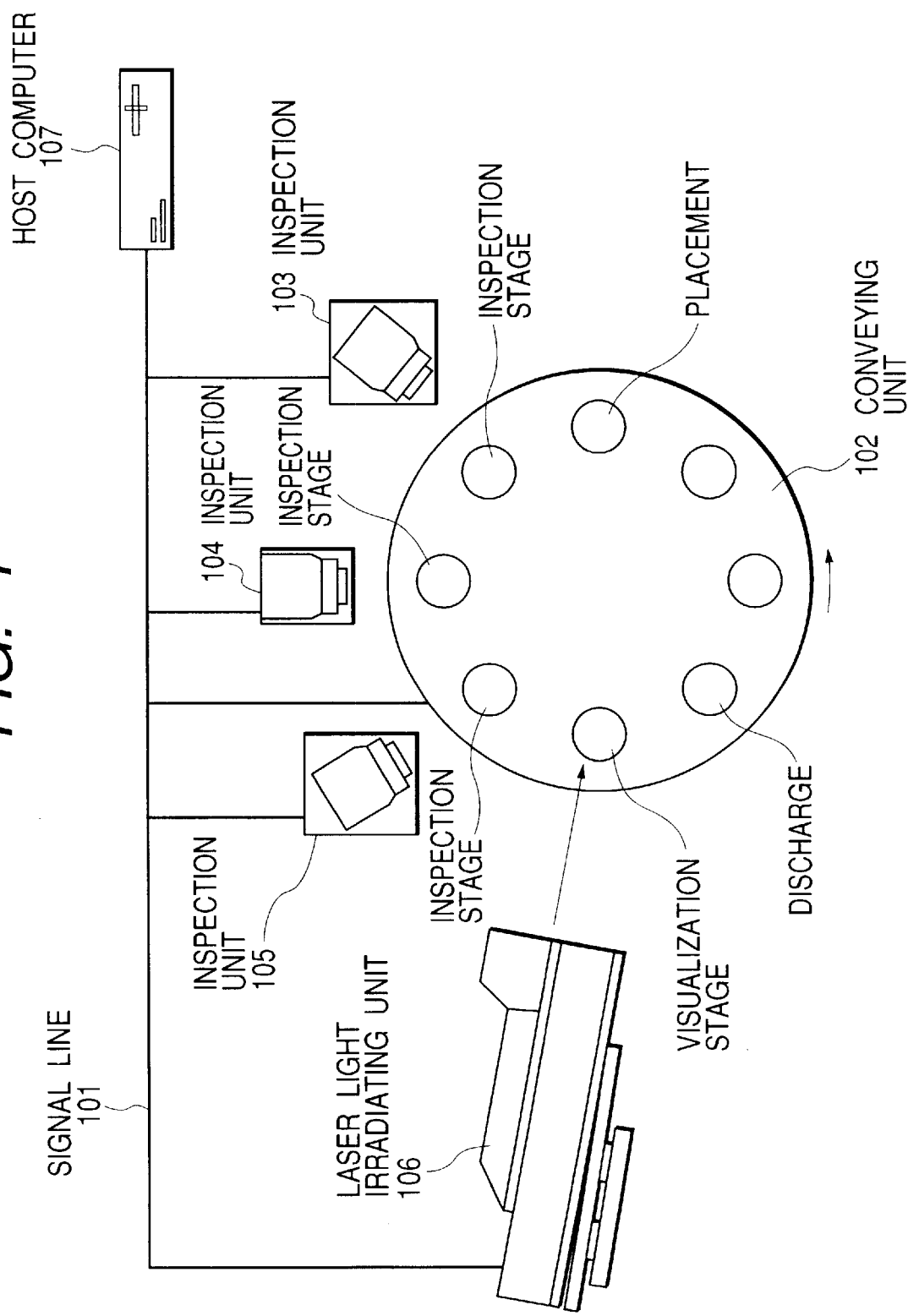
FIG. 1 is a block diagram showing the hardware configuration of a pre-viewing inspection device constituting an embodiment of the present invention.

In the present invention, in addition to the above-described requirements, it is preferred to discriminate whether the inspection article requires visual inspection or not, based on the detailed defect information generated by the detailed defect information generation step, and to visualize the detailed defect information on only the inspection article identified for the visual inspection.

More preferably the detailed defect information generated in the detailed defect information generation step includes defect position information, since the toil for detecting defects in the visual inspection can be effectively reduced.

The detailed defect information on the inspection article is preferably visualized in a non-used area of the inspection article. The non-used area means a non-image area if the inspection article is, for example, an electrophotographic photosensitive member as described later in more detail, or a non-charging area if the inspection article is a primary charging member or a transfer charging member. Stated differently, the non-used area in the present invention means an area not essential to exercising the functions of the inspection article.

The means for visualizing the detailed defect information on the inspection article is preferably a recording pen, an ink jet printer or a printing means utilizing laser light, in consideration of the stability of print and the design freedom of the visualizing means. Among these, the printing means utilizing laser light is particularly preferred for the reasons that finer printing is possible, there is no scattering of coloring material because coloring material such as ink is not used, and its maintenance is easy.

The detailed defect information to be visualized is represented preferably as briefly as possible, for example, by symbolizing the position, type, number, etc. of defects with numerals or patterns, as the space for visualization is limited.

The present invention is particularly effective when applied to an inspection article or a member having a function on the surface thereof, since the inspection can be sufficiently made without affecting the function. Such a tendency is particularly eminent when the inspection articles in the present invention are electrophotographic members in which the quality of the functional surface is directly linked with image quality, such as an electrophotographic photosensitive member, a primary charging member, a developer bearing member, an intermediate transfer member, a transfer charging member or a fixing member. Among these, in the electrophotographic photosensitive member, even a defect results in a serious detrimental effect, and the meritorious effects of the present invention are exhibited particularly conspicuously when such an electrophotographic photosensitive member is employed as the inspection article in the present invention.

In a case where the inspection article is an electrophotographic photosensitive member, it is preferred that the detailed defect information includes defect position information and is visualized in a non-image area in the longitudinal extension of the defect position derived from the defect position information.

The above-mentioned defect signal can be detected by the following methods, when the inspection article is an electrophotographic photosensitive member.

Japanese Patent Application Laid-Open Nos. 63-73139 and 7-218442, and Japanese Patent Nos. 2,935,881 and 2,967,291 disclose means for optically detecting a defect in a photosensitive layer installed in an electrophotographic photosensitive member. For optically identifying the defect in the electrophotographic photosensitive member, there is, for example, a method utilizing laser light. A laser beam emitted from a light source is converted by a beam expander into a parallel beam, irradiating the electrophotographic photosensitive member at an acute angle. If the electrophotographic photosensitive member is free of defect, the light is reflected at a constant angle in a parallel beam state. On the other hand, if the electrophotographic photosensitive member has a defect, the laser beam is scattered by such a defect whereby the reflected light is distorted. The reflected light is received by a photoelectric sensor and the difference between the incident light and the reflected light is photoelectrically converted to give an electrical signal, identifying the defect.

Also Japanese Patent Application Laid-Open No. 57-192847 and Japanese Patent Nos. 1,620,166 and 2,539,218 disclose methods for detecting a defect by a change in an electrical signal flowing in a photosensitive layer. For electrically identifying the defect in the electrophotographic photosensitive member, there is, for example, a method utilizing a high voltage source. A conductive charging roller is maintained in contact with the photosensitive layer, and a voltage according to the thickness of the film on the electrophotographic photosensitive member is applied while the charging roller and the electrophotographic photosensitive member are rotated in a synchronized manner. If the film is uniform in thickness and quality, the voltage resistance is uniform over the entire electrophotographic photosensitive member. However, if the film has a local fluctuation, the current flowing through the electrophotographic photosensitive member shows a change, or a leak in certain cases. Such changes are read to identify the defect.

These inspections give defect signals for spot-shaped defects, streak-shaped defects, bubble-shaped defects, scratches or deposits on the electrophotographic photosensitive member.

Now the present invention will be explained by an embodiment thereof, with reference to accompanying drawings.

As an embodiment of the present invention, there will be explained an example in which an electrophotographic photosensitive member constitutes the inspection article.

FIG. 1 is a view showing a pre-viewing inspection device for the electrophotographic photosensitive member, constituting an embodiment of the present invention.

A conveying unit 102 for the electrophotographic photosensitive member, inspection units (defect signal detection means) 103 to 105, and a laser light irradiating unit (detailed defect information visualizing means) 106 are connected with a host computer 107 through a signal line 101 and these units are controlled by the host computer 107 either directly or through another unit such as a sequencer or a controller.

If the inspection unit is an optical inspection unit, it is provided with a light source for irradiating the electrophotographic photosensitive member with light, a camera for detecting reflected light (defect signal) from the electrophotographic photosensitive member, and a computer for the optical inspection unit computer which processes the defect signals detected by the camera and transmits them to the host computer 107.

When the host computer 107 produces the detailed defect information (on the positions, types, number, etc. of defects) of the electrophotographic photosensitive member from the defect signal, the data transmitted from the optical inspection unit to the host computer 107 may be raw data originated from defects such as light scattering and information on the position at which that scattering occurs.

If the inspection unit is another type, for example, an electrical inspection unit, it is provided with a charger for applying a voltage to the electrophotographic photosensitive member, a current/voltage detector for detecting an electric current (defect signal) in the electrophotographic photosensitive member or the voltage (defect signal) in the voltage application thereto, and an electrical inspection unit computer for processing the defect signals detected by the detector and transmitting them to the host computer 107.

In order to obtain the defect position information by the use of the inspection unit, it may be provided with a position sensor such as an encoder for detecting the position in the electrophotographic photosensitive member. Naturally the position sensor need not be integrated with the inspection unit but can be provided separately.

The operation sequence from the pre-viewing inspection to the visual inspection will be explained below according to action of the units constituting the device, with reference to FIG. 1 and a flow chart (FIG. 2) of the pre-viewing inspection utilizing the pre-viewing inspection device of the present embodiment.

For clarifying the flow from the introduction into the pre-viewing inspection device to the visual inspection for the final judgment, FIG. 2 also shows the processes before and after steps 201 to 205 performed by a CPU 301 as explained later.

An electrophotographic photosensitive member introduced into the pre-viewing inspection device is mounted on a conveying unit 102.

The electrophotographic photosensitive member mounted on the conveying unit 102 is conveyed, by rotation thereof, to first to a position (hereinafter called inspection stage) at which the inspection is made by an inspection unit 103, and then to inspection stages by inspection units 104, 105 where optical or electrical inspections are performed by the inspection units 103 to 105 for the position or type of each of defects, thereby obtaining signals (defect signals) for the color (contrast), film state, electrical characteristics, etc. along with respective defect position signals (201 in FIG. 2).

For such inspections there can be adopted various inspecting methods such as an inspection on the color of the defect by irradiating the electrophotographic photosensitive member, rotated about its axis, with white light, introducing the reflected light into a photoelectric converting element such as a line sensor or a CCD camera and detecting a change in contrast, thereby identifying a normal portion and an abnormal portion, or an inspection on the film defect by irradiating the rotating electrophotographic photosensitive member with a laser beam at an acute angle, introducing the reflected light into a photoelectric converting element such as a line sensor or a CCD camera and detecting a change in film quality or film thickness from the distortion in the reflection angle, thereby identifying a normal portion and an abnormal portion, or an inspection on the electrical characteristics of the photosensitive layer by applying a voltage to the photosensitive layer by a corona charger or a charging roller and detecting the charging voltage or the current in the photosensitive layer.

In FIG. 1, three inspection stages for the inspection units 103 to 105 are employed respectively for the color (contrast), film state and electrical characteristics, but a plurality of inspections may be applied in a single inspection stage, depending on the inspecting light source, the layout of the photoelectric converting elements, and the range and items of the inspection.

Figure 2:
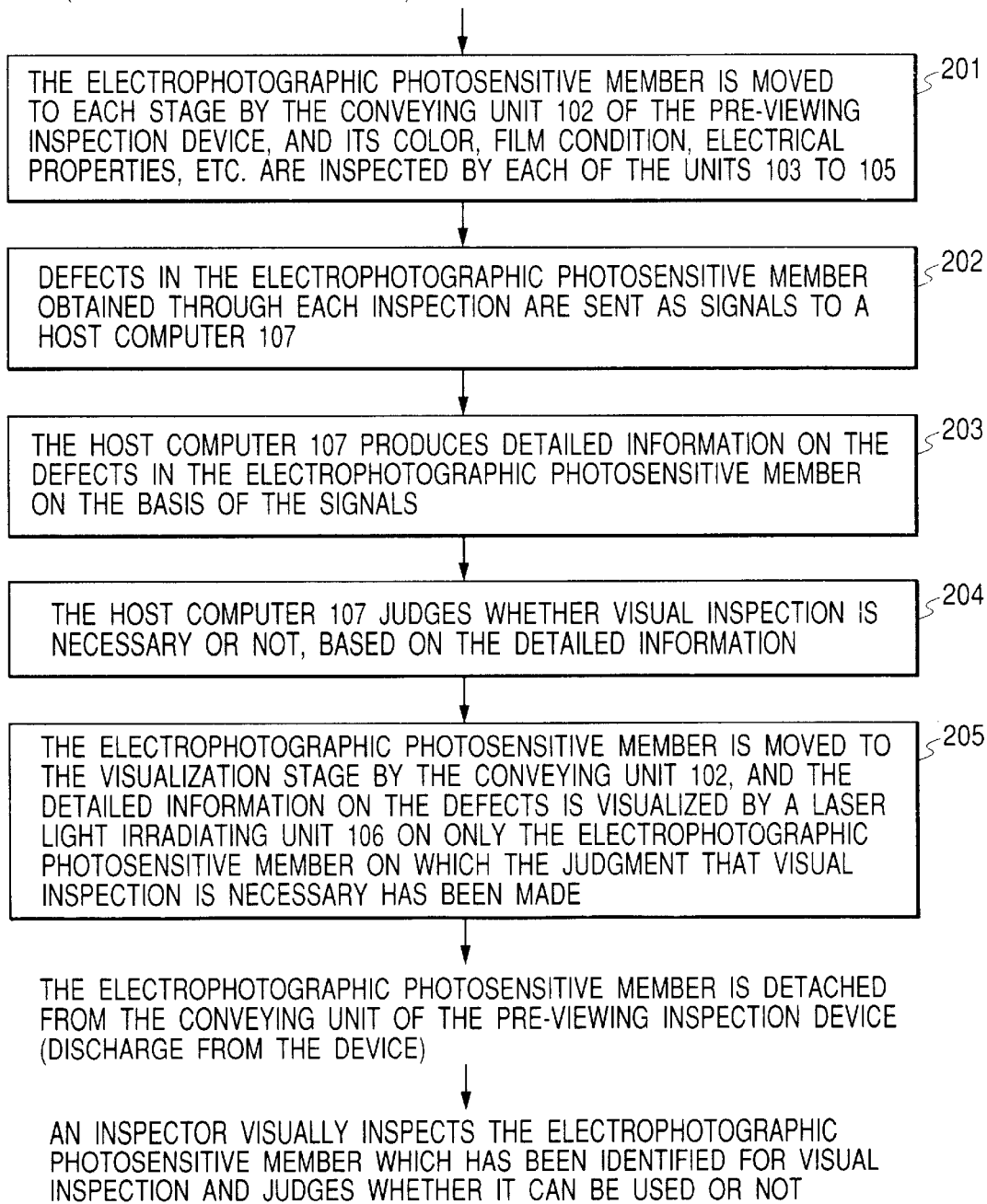
FIG. 2 is a flow chart showing the operation sequence of an embodiment of the present invention.

The defect signals, etc. are sent from the inspection units 103 to 105 to the host computer 107 (202 in FIG. 2).

Receiving the defect signals from the inspection units, the host computer 107 generates detailed defect information indicating, for example, which electrophotographic photosensitive member has what number and types of defects at which positions (203 in FIG. 2).

After generating the detailed defect information, the host computer 107 judges (determines), based on such detailed defect information, whether the electrophotographic photosensitive member can be used without practical problem and requires no visual inspection (visual inspection unnecessary) or whether the status of the electrophotographic photosensitive member cannot be determined and needs to be subjected to visual inspection (visual inspection necessary) (204 in FIG. 2).

Such determination is made through comparison with the database of defect criteria determined in advance and provided in the host computer.

Then, among the electrophotographic photosensitive members conveyed by the conveying unit 102 to a position (hereinafter called visualization stage) where the detailed defect information is visualized by a laser light irradiating unit (detailed defect information visualizing means) 106, only those judged as requiring the visual inspection are subjected to the visualization of the detailed defect information stored in the host computer (205 in FIG. 2).

The detailed defect information is visualized as character information as explained later, on a non-image area in an end portion of the electrophotographic photosensitive member, for example, by laser light of a carbon dioxide gas laser.

Figure 3:
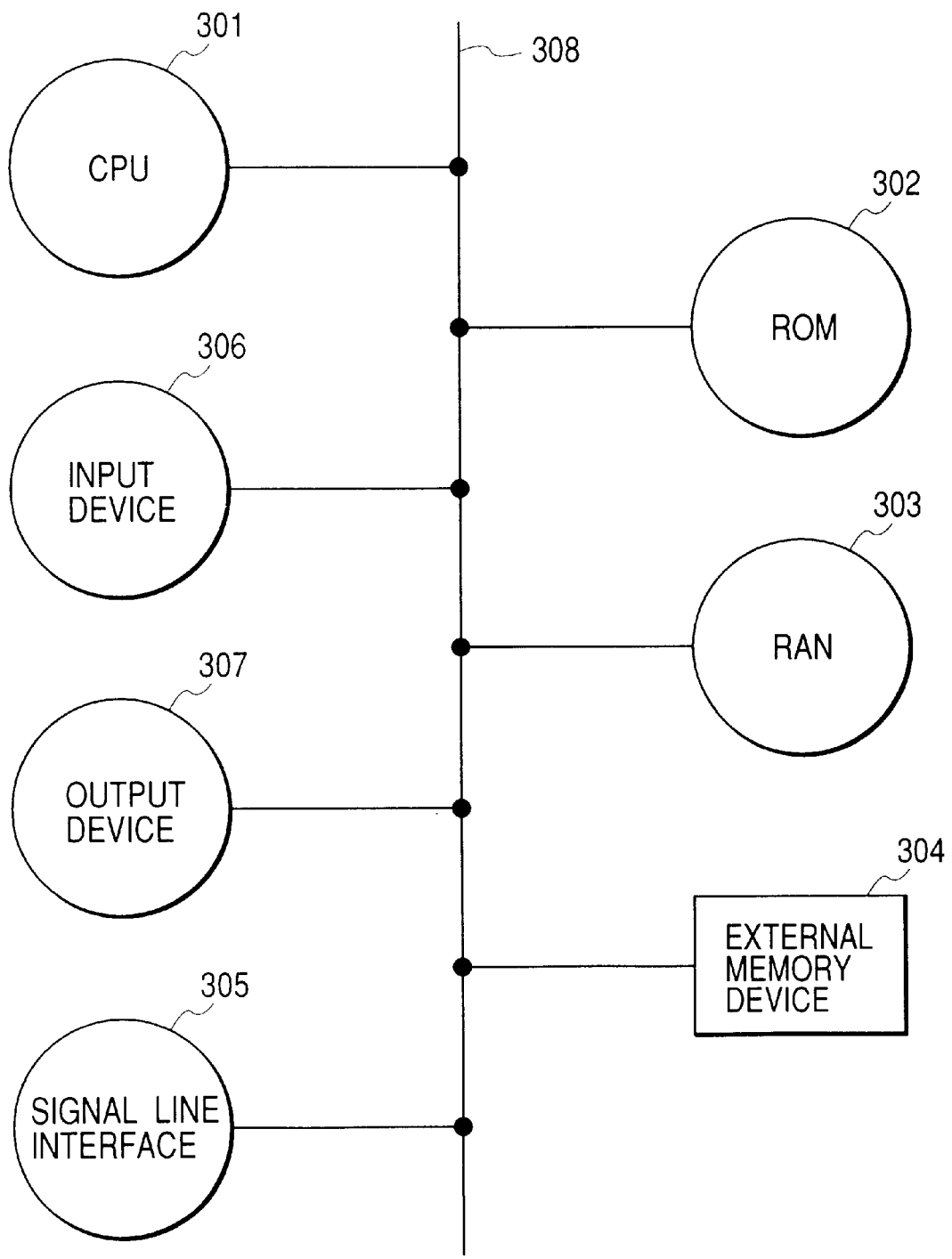
FIG. 3 is a block diagram showing the hardware configuration of a host computer in the pre view inspection device of an embodiment of the present invention.

FIG. 3 is a block diagram showing the hardware configuration of the host computer 107 in the embodiment 1 of the present invention.

A CPU 301 performs transmission, reception and coupling of data and controls components connected via a bus 308. Through the bus 308, address signals, control signals and various data among the components (devices) connected thereto are transferred. The CPU 301 carries out the aforementioned steps 201 to 205 shown in the flow chart in FIG. 2.

A ROM (read-only memory) 302 in advance stores a control sequence (computer program) for the CPU 301, which performs such a control sequence for realizing various processes such as data transmission and reception, and judgment on the electrophotographic photosensitive member. A RAM 303 is used as a work memory for the above-mentioned data transmission/reception and judgment and as a temporary memory for controlling various components.

An external memory device 304, capable of holding contents even when power supply is turned off, such as a hard disk, is used for storing a database, etc. An interface 305 connects the units shown in FIG. 1 with a signal line.

Figure 4:
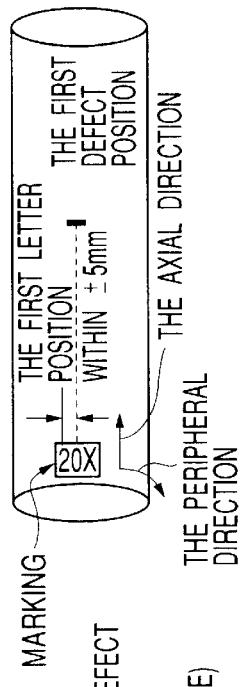
FIG. 4 is a view showing a print example of character (or letter) information on an electrophotographic photosensitive member and a specific example of character information in an embodiment of the present invention.

FIG. 4 shows an example of printing the character information on the electrophotographic photosensitive member and a specific example of the character information.

The character information is composed, as indicated by a print pattern 401, of a combination of three letters, in which the 1st letter indicates the position of a defect of the electrophotographic photosensitive member, the 2nd letter indicates the type of the defect, and the 3rd letter indicates the number of the defect.

The circumferential print position is, as indicated by a print position 402, at the end of the non-image area in a circumferential position corresponding to a worst defect among the detected defects.

The size of the printed letter can be arbitrarily selected, but is selected as 2×2 mm in the present example. Also the intensity of the laser beam and the spot diameter thereof are selected at suitable levels not causing sputtering or swelling around the printed portion.

For example, a character train "1●2" in a print example 403 indicates that "a dot-shaped defect (spot) exists in a coating area of ¹⁄₁₀ from the upper end of the coating area on the extension of the circumferential position of the character train and the number of defects is two in total, including a defect in another position".

The detailed defect information stored in the host computer 107 includes a serious defect not requiring visual inspection by an inspector in the later step, a slight defect on the boundary of usable/unusable judgment, an extremely trifle defect and even an erroneous detection by the defect signal detection means. For example, an electrophotographic photosensitive member (inspection article) having a serious defect may be discarded immediately after being discharged from the pre-viewing inspection device, thereby dispensing with visual inspection by an inspector. A sorting step for electrophotographic photosensitive members (inspection articles) to be discarded, electrophotographic photosensitive members (inspection articles) requiring visual inspection by an inspector and satisfactory electrophotographic photosensitive members (inspection articles) to be forwarded to a succeeding process, can be provided after discharge from the pre-viewing inspection device.

An electrophotographic photosensitive member thus sorted and printed is subjected to visual inspection by an inspector, thereby to determine whether it can be used or not in the final product.

Since the positions, number, types, etc. of defects can be known in advance from the detailed defect information visualized on the end portion of the electrophotographic photosensitive member, an inspector can very effectively perform the visual inspection and the presence of the defect information in advance prevents an error by overlooking, thereby achieving satisfactory accuracy of the inspection.

As explained in the foregoing, because of the increasing requirement for higher quality, the defects to be identified on inspection articles have become finer and finer, and unless the location of the defects is identified in advance, such defects are much more difficult to discover. The inspection method and apparatus of the present invention would bring about significant improvement in the efficiency and accuracy of the inspection step in which a major part of the toil has been concentrated in locating fine defects.

What is claimed is:

1. A pre-viewing inspection method for inspecting an inspection article prior to visual inspection thereof, the inspection article being an electrophotographic member, the method comprising:
    a defect signal detecting step of detecting a defect signal based on a defect state of the inspection article;
    a detailed defect information generating step of generating detailed defect information based on the defect signal detected in said defect signal detecting step, the detailed defect information including defect position information; and
    a detailed defect information visualizing step of selectively visualizing, on the inspection article, the detailed defect information generated in said detailed defect information generating step, said visualizing step including a printing step executed with a laser light,
    wherein said detailed defect information visualizing step visualizes the detailed defect information by printing the detailed defect information on a longitudinal extension of a defect position on the inspection article, based on the defect position information.

2. A method according to claim 1, further comprising:
    an inspection article judging step of determining, based on the detailed defect information generated in said detailed defect information generating step, whether or not the inspection article requires visual inspection;
    wherein said detailed defect information visualizing step visualizes the detailed defect information by printing only on an inspection article determined as requiring visual inspection in said inspection article judging step.

3. A method according to claim 1, wherein said detailed defect information visualizing step visualizes the detailed defect information by printing the detailed defect information in a non-used area of the inspection article.

4. A method according to claim 1, further comprising:
    a detailed defect information symbolizing step of symbolizing the detailed defect information generated in said detailed defect information generating step;
    wherein said printing step visualizes, the detailed defect information symbolized in said detailed defect information symbolizing step by printing the detailed defect information symbolized in said detailed defect information symbolizing step with the laser light.

5. A method according to claim 1, wherein the inspection article has functionality in all the surface thereof or in a part thereof.

6. A method according to claim 1, wherein the electrophotographic member is one selected from the group consisting of an electrophotographic photosensitive member, a primary charging member, a developer bearing member, an intermediate transfer member, a transfer charging member and a fixing member.

7. A method according to claim 6, wherein the electrophotographic member is an electrophotographic photosensitive member.

8. A method according to claim 7, wherein said detailed defect information visualizing step visualizes the detailed defect information by printing the detailed defect information in a non-image area of the electrophotographic photosensitive member.

9. A method according to claim 8, wherein said detailed defect information visualizing step visualizes the detailed defect information on a longitudinal extension of a defect position on the electrophotographic photosensitive member, based on the defect position information.

10. A method according to claim 1, wherein said defect signal detecting step is an optical defect signal detecting step including:
    a light irradiating step of irradiating the inspection article with light; and
    a reflected light detecting step of detecting reflected light from the inspection article irradiated with light in said light irradiating step.

11. A method according to claim 1, wherein said defect signal detecting step is an electrical defect signal detecting step including:
    a voltage applying step of applying a voltage to the inspection article; and
    a current/voltage detecting step of detecting an electric current in the inspection article subjected to voltage application in said voltage applying step or the voltage in said voltage applying step.

12. A pre-viewing inspection device for inspecting an inspection article prior to visual inspection thereof, the inspection article being an electrophotographic member, the device comprising:
    defect signal detecting means for detecting a defect signal based on a defect state of the inspection article;
    detailed defect information generating means for generating detailed defect information based on the defect signal detected by said defect signal detecting means, the detailed defect information including defect position information; and
    detailed defect information visualizing means for selectively visualizing, on the inspection article, the detailed defect information generated by said detailed defect information generating means, said visualizing means comprising printing means including a laser light,
    wherein said defect information visualizing means visualizes the detailed defect information by printing the detailed defect information on a longitudinal extension of a defect position on the inspection article, based on the defect position information.

13. A device according to claim 12, further comprising:
    inspection article judging means for determining, based on the detailed defect information generated by said detailed defect information generating means, whether or not the inspection article requires visual inspection;
    wherein said detailed defect information visualizing means visualizes the detailed defect information only on an inspection article determined as requiring visual inspection by said inspection article judging means.

14. A device according to claim 12, wherein said detailed defect information visualizing means visualizes the detailed defect information by printing the detailed defect information in a non-used area of the inspection article.

15. A device according to claim 12, further comprising:
   detailed defect information symbolizing means for symbolizing the detailed defect information generated by said detailed defect information generating means;
   wherein said visualizing means visualizes, the detailed defect information symbolized by said detailed defect information symbolizing means by printing the detailed defect information symbolized by said detailed defect information symbolizing means with the laser light.

16. A device according to claim 12, wherein the inspection article has functionality in all the surface thereof or in a part thereof.

17. A device according to claim 12, wherein the electrophotographic member is one selected from the group consisting of an electrophotographic photosensitive member, a primary charging member, a developer bearing member, an intermediate transfer member, a transfer charging member and a fixing member.

18. A device according to claim 17, wherein the electrophotographic member is an electrophotographic photosensitive member.

19. A device according to claim 18, wherein said detailed defect information visualizing means visualizes the detailed defect information by printing the detailed defect information in a non-image area of the electrophotographic photosensitive member.

20. A device according to claim 19, wherein said detailed defect information visualizing means visualizes the detailed defect information by printing the detailed defect information on a longitudinal extension of a defect position on the electrophotographic photosensitive member, based on the defect position information.

21. A device according to claim 12, wherein said defect signal detecting means is an optical defect signal detecting means including:
   light irradiating means for irradiating the inspection article with light; and
   reflected light detecting means for detecting reflected light from the inspection article irradiated with light by said light irradiating means.

22. A device according to claim 12, wherein said defect signal detecting means is an electrical defect signal detecting means including:
   voltage applying means for applying a voltage to inspection article; and
   current/voltage detecting means for detecting an electric current in the inspection article subjected to voltage application by said voltage applying means or the voltage applied by said voltage applying means.

* * * * *